United States Patent [19]

Hiestand et al.

[11] Patent Number: 4,885,933
[45] Date of Patent: Dec. 12, 1989

[54] HARDNESS IMPACT TESTER

[75] Inventors: Everett N. Hiestand, Galesburg; Stephen Balog, Kalamazoo, both of Mich.

[73] Assignee: The Upjohn Company, Kalamazoo, Mich.

[21] Appl. No.: 197,841

[22] Filed: May 24, 1988

[51] Int. Cl.⁴ ............................................. G01N 3/52
[52] U.S. Cl. ...................................................... 73/79
[58] Field of Search ............................................ 73/79

[56] References Cited

U.S. PATENT DOCUMENTS

| | | | |
|---|---|---|---|
| 3,548,645 | 12/1970 | Sikorski et al. | 73/79 |
| 3,669,261 | 6/1972 | Moulin | 73/79 |
| 4,011,447 | 3/1977 | Henderson | 377/20 |

OTHER PUBLICATIONS

Hiestand, E. N. and Smith, D. P., "Indices of Tableting Performance", 1984, pp. 145–159, Powder Technology (38).
"The Use of Tableting Indices to Study the Compaction Properties of Powders"—R. O. Williams, III and J. W. McGinity.
"Three Indices for Characterizing the Tableting Performance of Materials"–Hiestand and Smith.

Primary Examiner—Tom Noland
Assistant Examiner—Michele Simons
Attorney, Agent, or Firm—Flynn, Thiel, Boutell & Tanis

[57] ABSTRACT

A tester for testing hardness of a tablet formed from a compact of pharmaceutical powders. The tester has a spherical indenter suspended from a wire to impact the tablet to evaluate the hardness thereof. The tablet is contained in a split die holder which can regulate the die wall pressure. The indenter is supported against an electromagnet and, when released, swings through a controlled arc and impacts the tablet. The indenter passes three photocells in its downward arc toward the tablet, and the last photocell activates both a timing device connected to the first two photocells and a shutter plate to prevent reimpact of the indenter with the tablet face. After impact with the tablet face, the indenter is timed as it rebounds past the first two photocells. Since the distance between the first two photocells is known, the time it takes the indenter to travel between the first two photocells is sent to a computer and the velocity is calculated. The velocity is converted into rebound height of the indenter and, from this information, a calculation of the indentation hardness and the strain index is made.

11 Claims, 3 Drawing Sheets

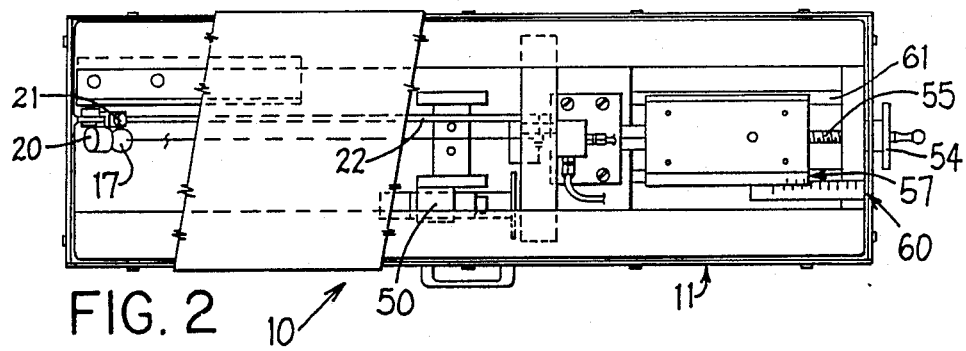
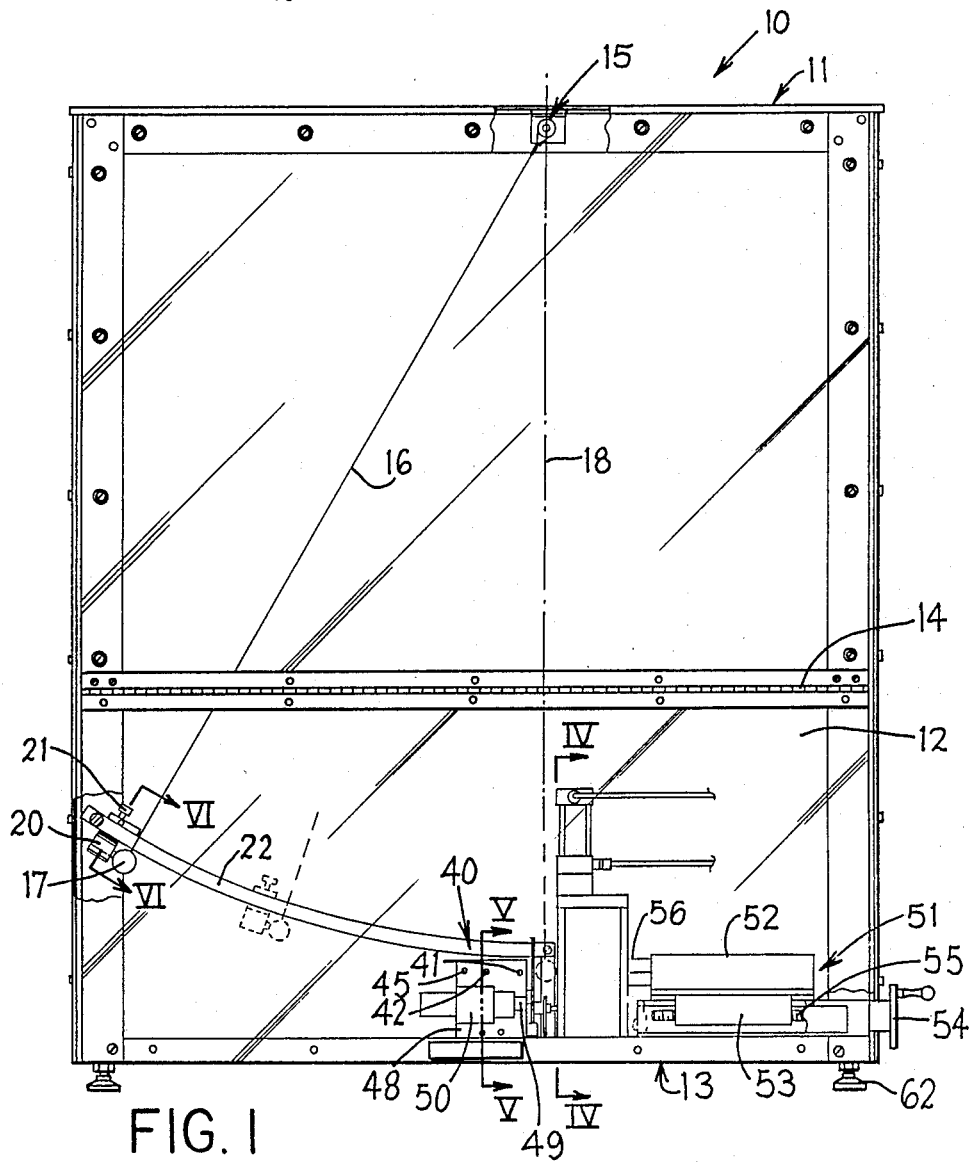

HARDNESS IMPACT TESTER

FIELD OF THE INVENTION

This invention relates to an improved apparatus for measuring the hardness of a compact or tablet of pharmaceutical powders.

BACKGROUND OF THE INVENTION

In the pharmaceutical industry, it is important to know the parameters which characterize the tableting properties of powders which are compressed to form tablets used for human and animal consumption. Of these parameters, the bonding index of the powder is probably the most important. This bonding index is determined from fundamental considerations of specific tablet models in order to determine how the inter-particle bonds form. With respect to the experimental tests which are carried out on these models, these typically involve an indentation hardness test wherein a spherical indenter is impacted against one face of the model, and a tensile strength determination wherein the model is subjected to transverse compression.

The hardness impact testers typically are of a pendulum type and comprise a ball or spherical indenter of known mass and diameter suspended from a wire, a tablet holding structure for maintaining the tablet in a fixed position during the test, and a device for determining the rebound height of the ball or spherical indenter after striking the tablet. The mass of the spherical indenter, the radius of the spherical indenter, the chordal radius of the dent produced in the tablet by impact with the spherical indenter, the initial height of the indenter and the rebound height of the indenter is then inserted into an equation in order to give the indentation hardness of the tablet.

In Powder Technology, 38 (1984) 145-159, Hiestand and Smith, there is disclosed an impact hardness tester which comprises a steel sphere suspended from a one-meter long steel wire, a die containing the compressed tablet mounted directly below the pendulum suspension point, and a polaroid camera for determining the rebound height of the spherical indenter after impact with the tablet. This apparatus also contains an electromagnet for holding and releasing the sphere and a shutter which when activated, prevents a second impact of the sphere against the tablet.

With this early model impact hardness tester, it is difficult to accurately determine the rebound height of the sphere from the time-lapse photographs. Also the tablet is subject to fracture upon impact by the sphere, which fracture can dissipate some of the energy of the sphere and, therefore, decrease the rebound height and yield incorrect values in the calculations of the dynamic indentation hardness and the strain index.

A further pendulum-type hardness impact tester is described in an article by R. 0. Williams III, and J. W. McGinity. This latter impact hardness tester modified the basic apparatus described by Hiestand and Smith by substituting a ballistic sensor for the polaroid camera to measure the velocity of the sphere before and after impact with the tablet. This latter tester also uses a split die assembly to minimize triaxial decompression of the tablet during the hardness test. Although these modifications do improve the operation of the impact hardness tester, the basic problems with the apparatus are still unresolved.

More specifically, the ballistic sensor measures the velocity of the spherical indenter by timing the interruption caused by the equator of the spherical indenter passing between a solid state infrared light source and a detector. The time of this interruption and the diameter of the sphere are then used to compute the velocity of the sphere. This necessitates the adjustment of the ballistic sensor each time a spherical indenter of a different diameter is used, and also introduces an additional calculation to be made in the determination of the hardness of the tablet. Furthermore, although the split die arrangement for holding the tablet helps alleviate the fracture problems, nevertheless undesirable fractures still occur.

Accordingly, it is an object of this invention to provide an improved pendulum-type impact hardness tester for measuring the hardness of tablets or compacts from a powdered material, which impact hardness tester improves upon the performance characteristics of the known impact hardness testers described above.

More specifically, the improved hardness impact tester has an improved split die assembly which has an upper die portion connected to a pressure cylinder which enables the regulation of the die wall pressure. The improved impact hardness tester also contains an improved rebound height detector which comprises photocells for determining the rebound velocity of the spherical indenter after impact with the tablet.

Other objects and purposes of the invention will be apparent to persons familiar with impact hardness testers of this general type upon reading the following specification and inspecting the accompanying drawings.

BRIEF DESCRIPTION OF THE DRAWINGS

FIG. 1 a front elevational view of the impact tester according to this invention;

FIG. 2 is a top view thereof;

Figure 3:
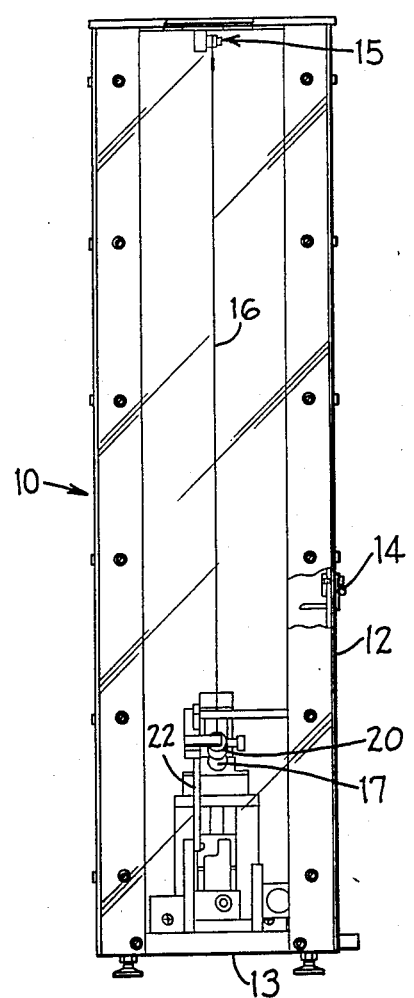
FIG. 3 is a side elevational view thereof.

Certain terminology will be used in the following description for convenience in reference only, and will not be limiting. For example, the words "upwardly", "downwardly", "rightwardly" and "leftwardly" will refer to directions in the drawings in which references are made. The words "inwardly" and "outwardly" will refer to directions toward and away from, respectively, the geometric center of the impact hardness tester and designated parts thereof. Said terminology will include the words specifically mentioned, derivatives thereof, and words of similar import.

DETAILED DESCRIPTION

FIGS. 1 through 3 illustrate therein a pendulum-type impact hardness tester apparatus 10 according to the present invention for testing the hardness of a tablet or compact 27 made from a powdered material. This tester 10 includes a hollow boxlike frame or housing 11. The side walls of the housing are preferably of a transparent material in order to enable an operator to view the operation of the tester 10. The front side of the frame 11 has a lower door 12 which is hinged at 14 to enable an operator to access the equipment enclosed in the housing by opening the door upwardly about the hinge 14.

Fixed adjacent the housing top wall is a suspension point or pin 15 for an elongated steel wire 16 having a spherical indenter 17 releasably affixed to the lower end thereof. The steel wire 16 and spherical indenter 17 constitute a pendulum which is constrained to swing in a controlled arc between operational and non-operational positions. The wire 16 has a known length and the spherical indenter 17 is a steel ball of known diameter and mass.

Figure 6:
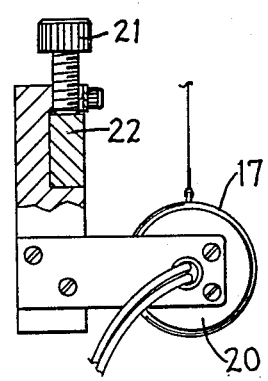
FIG. 6 is an enlarged, fragmentary sectional view as taken along line VI-VI in FIG. 1 and showing the spherical impacter hold-release assembly.

The spherical indenter 17 is maintained in a non-operational position by a holding device 20, specifically an electromagnet, which maintains the spherical indenter 17 at a desired elevational position prior to the commencement of the test. As shown in FIGS. 1 and 6, the holding device 20 is affixed to an elongated scale 22 which is attached to the leftward side of the frame 11. The scale 22 is of arcuate configuration generated about the suspension or pivot point 15. Scale 22 has indicia, in degrees, marked thereon in order to determine the initial setting or position of the spherical indenter. The electromagnet 20 is releasably locked on the scale 22 at a selected position by a positioning screw 21 which engages the scale 22. The electromagnet 20 may be positioned at any desirable position along the scale 22 by loosening the positioning screw 21, sliding the electromagnet 20 along the scale 22 to a desired position, and then retightening the positioning screw 21.

Figure 4:
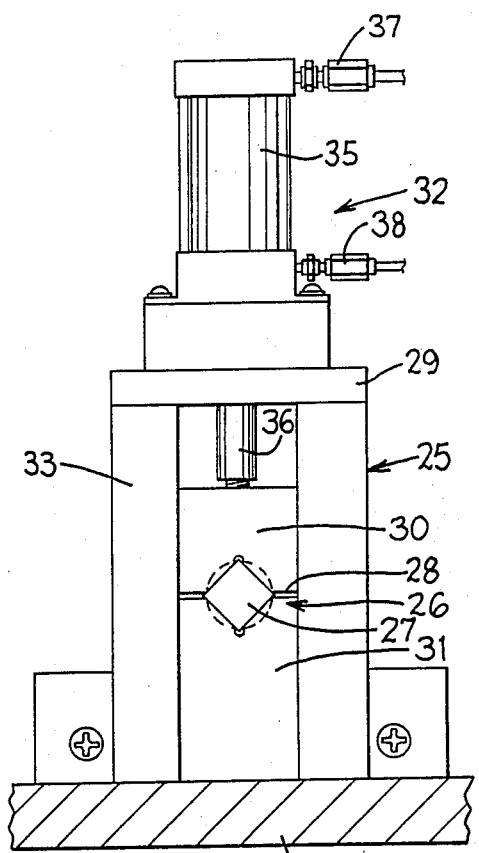
FIG. 4 is an enlarged side elevational view of the die assembly taken along line IV-IV in FIG. 1.

The impact hardness tester 10 also includes a tablet holding structure 25 affixed to the bottom wall of the housing in such a manner that the vertical face of the tablet 27, which face is impacted, is positioned closely adjacently or within a vertical plane 18 containing therein the axis of the suspension point 15. The tablet holding structure 25, as shown in FIG. 4, includes a split die tablet holder 26 which is adapted to hold the tablet 27. The split die tablet holder 26 includes an upper die portion 30, which is affixed to a piston 36 of a fluid pressure cylinder 35, and a lower die portion 31 which bears on the housing base 13. These die portions 30 and 31 define therebetween an opening 28 for accommodating the tablet 27, which opening 28 is split diagonally of the tablet.

The fluid pressure cylinder 35 has its housing mounted on a top plate 29 which is fixedly secured to the base 13 through plural support legs 33 wherein the piston rod 36 slidably extends downwardly for connection to the top die portion 30. These support legs also confine the die portions therebetween. Pressure fluid is supplied to the cylinder by the connections 37 and 38. The fluid pressure cylinder 35 enables the die wall pressure applied to the tablet 27 to be maintained at a desired pressure by controlling the amount of pressure applied to the upper split die portion 30 by the fluid pressure cylinder piston 36. By controlling the amount of pressure applied to the tablet 27, fractures of the tablet 27 upon impact with the spherical indenter 17 can be minimized.

Figure 5:
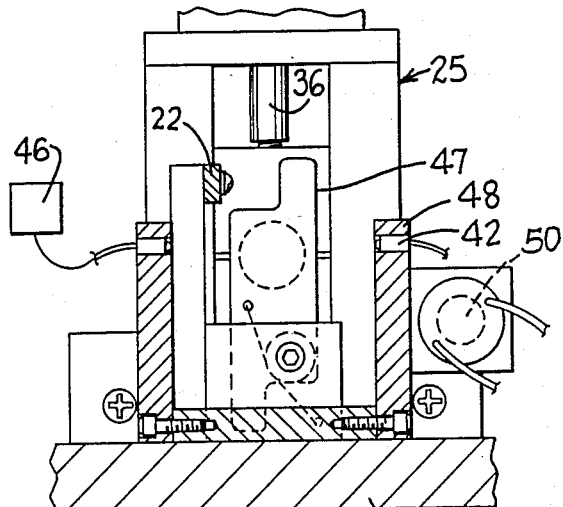
FIG. 5 is an enlarged, fragmentary side elevational view as taken along line V-V in FIG. 1 and showing of the die and shutter assembly.
Figure 7:
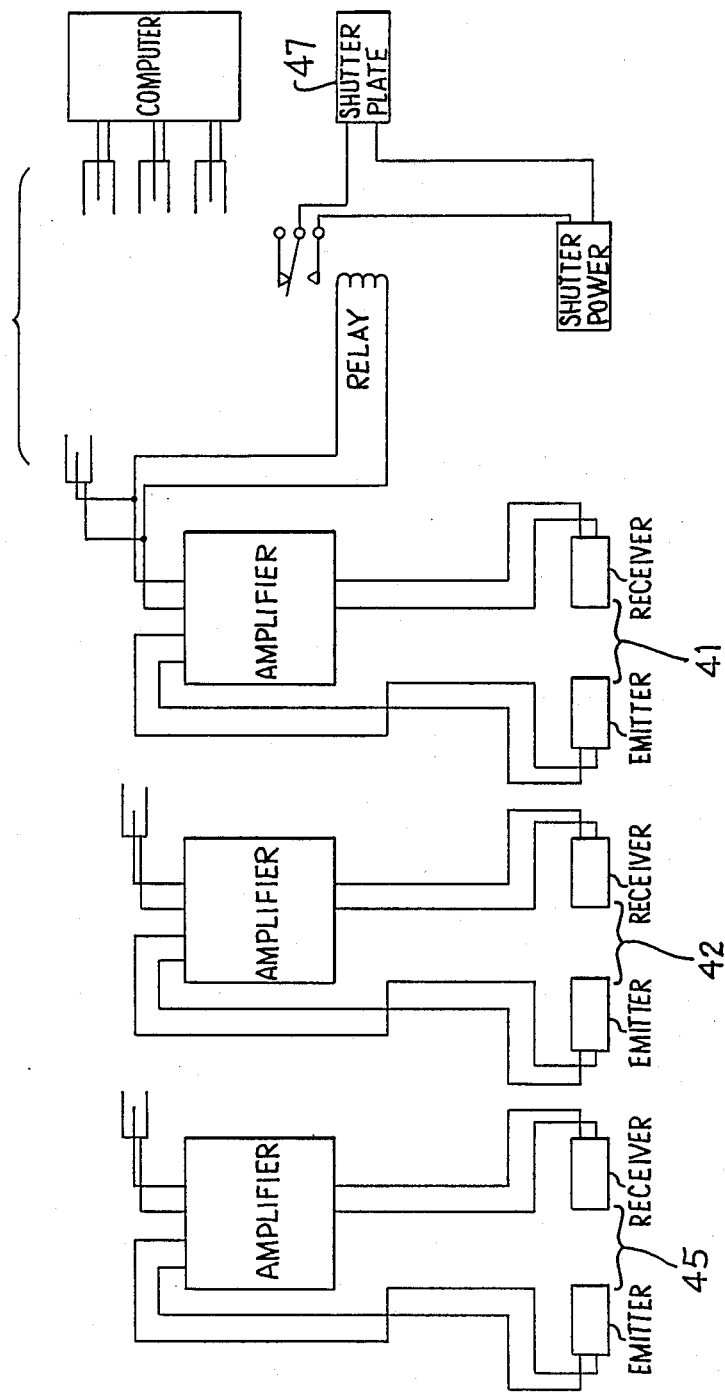
FIG. 7 schematically illustrates the circuitry associated with the photocells.

Also attached to the frame base 13 is a rebound height sensor 40 which includes a first photocell 41, a second photocell 42 and a third photocell 45. As shown in FIG. 5, the photocells 41, 42 and 45 are held in plural support plates 48 which are releasably secured to the frame base 13 and are positioned such that the spherical indenter will pass between them during its downward swing. Each photocell is conventional and includes a light emitter, a light receiver and associated circuitry. The three photocells are positioned at spaced points along the arcuate path of the spherical indenter 17. The first photocell 41, which is positioned closest to the vertical plane 18, functions to activate the second and third photocells 42 and 45 upon detection of the downward swinging movement of the spherical indenter 17. The second and third photocells 42 and 45 are positioned a known distance apart along the arcuate path, and are connected to a monitoring device 46 such as a conventional digital storage oscilloscope or an electronic timer or both. The monitoring device 46 measures the difference between (1) the time of the interruption of the light between the light emitter and receiver at the second photocell 42 and (2) the time of the interruption of the light between the light emitter and receiver at the third photocell 45. With the distances between the second and third photocells 42 and 45 being known, the difference between the times of interruption at the second and third photocells is then used to calculate the rebound velocity of the spherical indenter 17 after it has impacted with the tablet 27. By knowing the rebound velocity of the spherical indenter 17 after impact with the tablet 27, the rebound height of the spherical indenter 17 can be calculated.

The first photocell 41 also activates a relay to a shutter plate restrainer 50 that releases a shutter plate 47, as shown in FIG. 5, that prevents reimpact of the spherical indenter 17 with the tablet 27. The shutter plate 47 is a spring-activated metal plate that is positioned on the frame base 13 and closely adjacent to the vertical plane 18. The shutter plate restrainer is a solenoid actuated device which retracts a piston 49 which is restraining the shutter plate 47 upon receipt of a signal from the first photocell 41. After completion of the test, the shutter plate 47 is lowered and the piston 49 extended to maintain the shutter plate 47 in a lowered position.

Because the rebound height sensor 40 of the present invention determines the rebound height of the spherical indenter 17 by determining the time it takes the spherical indenter 17 to pass from the second photocell 42 to the third photocell 45, no adjustments need be made to the system when varying the diameter of the spherical indenter 17. Another added feature of this particular type of arrangement is that the velocity readout of the rebound height sensor 40 can be sent directly to a computer in order to determine the hardness of a tablet.

The impact hardness tester 10 also includes a tablet positioning structure 51 affixed to the base 13. The tablet positioning structure 51 includes an upper slide portion 52 having a piston 56 affixed thereto and a bottom portion 53. The piston 56 projects into the rear end of the tablet opening 28 and is of the same shape and orientation so as to function as a rigid bearing engagement with the rear face of the tablet. The bottom portion 53 is slidingly supported on parallel rods or ways 61 which are stationarily mounted on the base. A manually rotatable crank 54 drives a screw shaft 55 which is engaged with the portion 53.

As shown in FIG. 2, the use of a scale 57 provided on the tablet positioning structure upper portion and a scale 60 provided on the tablet positioning structure bottom portion enables the distance which the tablet positioning structure upper portion piston 56 is advanced into the tablet holding structure 25 to be carefully monitored. The piston 56 engages with the back surface of the tablet 27 and is positioned so that the tablet front face is flush with the front face of the split die tablet holder 26 and positioned substantially within the vertical plane so that the spherical indenter 17 will impact the tablet 27 at a position directly vertical below the suspension point 15.

Leveling legs 62 are provided on the frame base 13 in order to maintain the impact hardness tester 10 at a level position during testing of the hardness of the tablet 27.

OPERATION

The operation of the impact hardness tester will be briefly described to insure a thorough understanding thereof.

The tablet 27 to be tested is placed in the split die tablet holder 26. The piston 56 is advanced so that the tablet front face is flush with the die front face. The die wall pressure is also adjusted to a desirable amount by the fluid pressure cylinder 32, with some die wall pressure being applied before the tablet front face is aligned flush with the die front face. The spherical indenter 17 is held against the pointed tip of the core of the electromagnet 20 and its position stabilized by imposing thereon both an a.c. signal on a d.c. signal to gently vibrate the spherical indenter to bring it to an "equilibrium" position. The a.c. signal is first removed, and then the d.c. signal is interrupted so that the spherical indenter is released and swings down so as to strike the front face of the tablet or compact.

The split die tablet holder 26 is mounted substantially directly below the suspension point 15, with the front faces of the tablet 27 and split die holder being slightly horizontally displaced from the vertical plane 18 so that the center of the indenter 17, when the indenter tangentially contacts the front tablet face, is disposed within this plane. The face of the tablet 27 is exposed by way of the opening 28. The regulation of the die wall pressure in the tablet holder 26 by the fluid pressure cylinder 32 minimizes the occurrences of fractures during the impact test.

The second photocell 42 and the third photocell 45 do not monitor the downward swinging movement of the spherical indenter. However, when the downward swinging spherical indenter passes the first photocell 41, a monitoring device is activated. This monitoring device may be a digital storage oscilloscope or an electronic timer, or both, connected to the second and third photocells 42 and 45. The output from the first photocell 41 is also used to activate a relay to a shutter plate restrainer 50 which releases the shutter plate 47 so that it swings upwardly in front of the tablet to prevent reimpact of the spherical indenter 17 with the tablet 27. The mechanical response of releasing the shutter plate 47 is slow enough to permit the spherical indenter 17 to impact the tablet 27 and rebound out of the way before the shutter plate 47 is fully extended.

After impact with the tablet, the spherical indenter 17 first passes the second photocell 42 and then passes the third photocell 45. The time which it takes the spherical indenter 17 to interrupt the third photocell 45, after having interrupted the second photocell 42 is measured. With the distance between the third and second photocell being known, this time is used to calculate the velocity of the spherical indenter 17 and thereby calculate its rebound height.

The timer provides an electrical output that can be sent directly to a computer. Thus the computer can be programmed to do the calculations. The initial height of the indenter 17 can be placed in the memory, the rebound signals are converted to rebound height, and an operator need only enter the chordal radius of the dent in the tablet in order to supply all the information needed to make the calculations of indentation hardness and strain index.

Although a particular preferred embodiment of the invention has been disclosed for illustrative purposes, it will be recognized that variations or modifications of the disclosed apparatus, including the rearrangement of parts, and the substitution of equivalent lie within the scope of the present invention.

The embodiments of the invention in which an exclusive property or privilege is claimed are defined as follows:

1. A pendulum-type tablet impact tester for measuring the hardness of a tablet used in pharmaceutical applications, said impact tester comprising:
    a steel sphere constrained by a wire to swing through a controlled arc and strike a tablet held in a fixed position;
    an electromagnet for maintaining said steel sphere at an initial height at the top of said controlled arc and releasing said steel sphere when a release signal is applied to it;
    a split die for maintaining said tablet in a fixed position, said split die defining an interior space into which said tablet is inserted and having a top portion and a bottom portion;
    variable pressure means connected to said top portion of said split die enabling the pressure of the die walls as applied to the tablet to be adjusted to a desired amount;
    shutter means for preventing said steel sphere from restriking said tablet;
    first sensing means comprising a first photocell receiver and a light emitter for activating a monitoring device and said shutter means upon detection of said steel sphere swinging downward through said controlled arc, said monitoring device being one or more members selected from the group consisting of a digital storage oscilloscope and an electrode timer; and
    second sensing means comprising a second photocell receiver and light emitter and a third photocell receiver and light emitter, said second sensing means being capable of calculating the velocity of the steel sphere after it strikes the tablet by monitoring the amount of time it takes for the steel sphere to travel from said second photocell receiver and light emitter to said third photocell receiver and light emitter.

2. The pendulum tablet impact tester of claim 1 comprising a computer in combination with said second sensing means.

3. A pendulum-type tablet impact tester for measuring the hardness of a tablet used in pharmaceutical applications, said impact tester comprising:
    a steel sphere constrained by a wire to swing through a controlled arc and strike a tablet held in a fixed position;
    an electromagnet for maintaining said steel sphere at an initial height at the top of said controlled arc and releasing said steel sphere when a release signal is applied to it;
    a split die for maintaining said tablet in a fixed position, said split die defining an interior space into which said tablet is inserted and having a top portion and a bottom portion;

variable pressure means comprising an air cylinder connected to said top portion of said split die for enabling the pressure of the die walls as applied to the tablet to be maintained at a desired amount;

first sensing means comprising a first photocell receiver and a light emitter for activating a monitoring device upon detection of said steel sphere swinging downward through said controlled arc, said monitoring device being one or more members selected from the group consisting of a digital storage oscilloscope and an electronic timer; and second sensing means comprising a second photocell receiver and light emitter and a third photocell receiver and light emitter, said second sensing means being capable of calculating the velocity of the steel sphere after it strikes the tablet by monitoring the amount of time it takes for the steel sphere to travel from said second photocell receiver and light emitter to said third photocell receiver and light emitter.

4. The pendulum table impact tester of claim 3 comprising a computer in combination with said second sensing means.

5. The pendulum tablet impact tester of claim 3 comprising shutter means for preventing said steel sphere from restriking said tablet.

6. A pendulum-type tablet impact tester for measuring the hardness of a tablet used in pharmaceutical applications, said impact tester comprising:

a spherical indenter adapted to swing through a controlled arc and strike a tablet held in a fixed position;

indenter positioning means for maintaining said spherical indenter at an initial height at the top of said controlled arc and for releasing said spherical indenter when a release signal is applied to it;

tablet positioning means for maintaining said tablet in a fixed position, said tablet positioning means comprising a split die having variable die wall pressure controlling means;

shutter means for preventing said spherical indenter from restriking said tablet;

first sensing means comprising a photocell for activating a monitoring device and said shutter means upon detection of the spherical indenter swinging through said controlled arc; and second sensing means comprising a pair of photocells spaced along said arc for calculating the velocity of the spherical indenter after it has struck the tablet.

7. The impact tester of claim 6, wherein said indenter positioning means comprises an electromagnet.

8. The impact tester of claim 6, wherein said split die is divided into top and bottom portions and said variable die wall pressure controlling means comprises a fluid pressure cylinder connected to the top portion of the split die.

9. The impact tester of claim 6, wherein the monitoring device activated by the first sensing means is one or more members selected from the group consisting of a digital storage oscilloscope and an electronic timer.

10. The impact tester of claim 6, wherein the shutter means comprises a mechanical gate.

11. The impact tester of claim 6, wherein said spherical indenter comprises a steel sphere connected to a wire.

* * * * *

UNITED STATES PATENT AND TRADEMARK OFFICE
CERTIFICATE OF CORRECTION

PATENT NO. : 4 885 933

DATED : December 12, 1989

INVENTOR(S) : Everett N. Hiestand, et al

It is certified that error appears in the above-identified patent and that said Letters Patent is hereby corrected as shown below:

Column 6, line 32; after "die" insert ---for---. (1st occurrence)

line 43; change "electrode" to ---electronic---.

Signed and Sealed this

Twenty-first Day of May, 1991

Attest:

HARRY F. MANBECK, JR.

Attesting Officer     Commissioner of Patents and Trademarks